United States Patent [19]

Stief et al.

[11] Patent Number: 5,512,449
[45] Date of Patent: Apr. 30, 1996

[54] METHOD FOR THE FUNCTIONAL DETERMINATION OF PROTEIN C INHIBITOR

[75] Inventors: Thomas Stief; Norbert Heimburger; Klaus-Peter Radtke, all of Marburg, Germany

[73] Assignee: Behringwerke Aktiengesellschaft, Marburg, Germany

[21] Appl. No.: 352,683

[22] Filed: Nov. 30, 1994

Related U.S. Application Data

[63] Continuation of Ser. No. 958,475, Oct. 8, 1992, abandoned, which is a continuation of Ser. No. 758,368, Sep. 10, 1991, abandoned, which is a continuation of Ser. No. 158,946, Feb. 19, 1988, abandoned.

[30] Foreign Application Priority Data

Feb. 23, 1987 [DE] Germany ................... 37 05 744.8

[51] Int. Cl.$^6$ .................. C12Q 1/56; C12Q 1/37; C12N 9/99
[52] U.S. Cl. .................. 435/13; 435/23; 435/184; 436/69
[58] Field of Search .................. 435/13, 23, 184; 436/69

[56] References Cited

U.S. PATENT DOCUMENTS

| | | | |
|---|---|---|---|
| 3,931,399 | 1/1976 | Bohn et al. | 425/105 |
| 4,818,690 | 4/1989 | Pâques | 435/13 |
| 5,057,414 | 10/1991 | Stief | 435/13 |
| 5,358,932 | 10/1994 | Foster | 514/12 |

FOREIGN PATENT DOCUMENTS 8600413  1/1986  WIPO ..................... 435/13

OTHER PUBLICATIONS

Thrombosis Haemostasis, 56: 415–416 (1986).
The Merck Index, ninth edition (1976), pp. 4510–4511.
M. Geiger et al, "Functional Assays for Protein C Activity and Protein C Inhibitor Activity in Plasma", *Thrombosis and Haemostasis,* vol. 61, No. 1, pp. 86–92 (1989).

T. Stief et al, "Evidence for Identity of PCI and Plasminogen Activator Inhibitor 3" *Biol. Chem. Hoppe–Seyler,* vol. 368, pp. 1427–1433, Oct. 1987.

K. Suzuki et al, "Mechanism of Inhibition of Activated Protein C by Protein C Inhibitor", *J. Biochem,* vol. 95, No. 1, pp. 187–195 (1984).

Suzuki, et al, "Protein C Inhibitor," The Journal of Biological Chemistry, vol. 258, No. 1, Jan. 10, pp. 163–168, 1983.

Geiger et al. "Activated Protein C and Urokinase (UK) . . . " *Circulation* (Oct. 1986) 74: II–234.

Geiger et al. "Functional Characterization of Protein . . . " *Thrombosis Haemostasis (Jul. 6, 1987) 58: 277.*

Heebe et al "Immanological Similarities Between . . . " (Jul. 6, 1987) *Thombosis Haemostasis* 58:277.

Heebe et al. "Immunological Identity of Heparin–dependent Plasma . . . " Journal of Biological Chemistry 262:15813–16 1987.

Verheijen et al. "Extrinsic Plasminogen Activator and Urokinase" *Methods of Enzymatic Analysis* vol. V pp. 425–433 (1984).

Stump et al. "Purification and Characterization of a . . . " *Journal of Biological Chemistry* (1986) 261: 12759–66.

Primary Examiner—Ralph J. Gitomer
Attorney, Agent, or Firm—Finnegan, Henderson, Farabow, Garrett & Dunner

[57] ABSTRACT

A method and an agent for the functional determination of protein C inhibitor in body fluids are described, in which this fluid is incubated with a known amount of a plasminogen activator, fibrinogen and a sulfated carbohydrate, and the residual activity of the plasminogen activator is determined, and from this the amount of protein C inhibitor is determined.

9 Claims, No Drawings

METHOD FOR THE FUNCTIONAL DETERMINATION OF PROTEIN C INHIBITOR

This application is a continuation of application Ser. No. 07/958,475 filed Oct. 8, 1992, now abandoned, which is a continuation of application Ser. No. 07/758,368 filed Sep. 10, 1991, now abandoned, which is a continuation of application Ser. No. 07/158,946 filed Feb. 19, 1988, now abandoned.

The invention relates to a method for the determination of the protein C inhibitor activity in a liquid ("funconal determination of protein C inhibitor"), in which protein C inhibitor acts on an amount of plasminogen activator of known activity and inhibits part of this activity, and the protein C inhibitor activity is determined from the residual activity of plasminogen activator by addition of a chromogenic substrate in such a way that the change in the extinction produced by the appearance of the chromophore is measured using a spectrophotometric method.

Protein C inhibitor inhibits activated protein C. Activated protein C, a vitamin K-dependent serine protease, is produced when protein C is activated by the thrombin/thrombomodulin complex during the activation of coagulation. Protein C is the central protein in one of the most important mechanisms of hemostasis regulation. On the one hand, activated protein C reduces the rate of formation of thrombin by inactivating coagulation factors F Va and F VIIIa. On the other hand, it stimulates fibrinolysis. Both the anticoagulant and the profibrinolytic functions of protein C are controlled by protein C inhibitor, which thus has an import ant function in controlling anticoagulation and fibrinolysis. This why functional determination of protein C inhibitor is of great importance. State of the art functional determinations of protein C inhibitor make use of a method utilizing the inhibitory action of protein C inhibitor on activated protein C (J. Biol. Chem. 258 (1) 163–168, 1983).

It has now been found, surprisingly, that protein C inhibitor inhibits not only activated protein C but also the plasminogen activators urokinase and tissue plasminogen activator. The inhibition of the plasminogen activators is accelerated in the presence of heparin or another polysulfated polysaccharide.

Other sulfated carbohydrates include dermatan sulfate, dextran sulfate, chondroitin sulfate, pentosan sulfate, galactosan polysulfate, keratan sulfate or mucopolysaccharide polysulfate.

The concentration of the sulfated carbohydrate can be $10^{-8}$ to 1 mg/ml.

It has additionally been found, surprisingly, that the plasminogen activators urokinase and tissue plasminogen activator, preferably urokinase, can be used in place of activated protein C for the diagnostic determination of protein C inhibitor.

It has also been found that, when the method according to the invention is used, it is possible to carry out the protein C inhibitor determination in plasma if the inhibition, which is likewise catalyzed by heparin or another polysulfated polysaccharide, of urokinase by antithrombin III is eliminated. It has been found, surprisingly, that this can be achieved by addition of fibrinogen to the reaction mixture, replacement of heparin by dextran sulfate or pentosan sulfate, and carrying out the incubation or pentosan sulfate, and carrying out of the plasminogen activator at 5°–40° C., preferably 10°–30° C., particularly preferably 230° C. Under these reaction conditions, the inhibition of urokinase by protein C inhibitor takes place with the same rate as when heparin is used as cofactor.

Hence the invention relates to a method for the functional determination of protein C inhibitor in a body fluid, which comprises incubation of this fluid with a known amount of a plasminogen activator in the presence of fibrinogen, and heparin or a polysulfated polysaccharide, preferably dextran sulfate, and determination of the residual activity of the plasminogen activator, and from this the amount of protein C inhibitor. The determination can be carried out at 20°–25° C.

Tissue plasminogen activator or urokinase, preferably urokinase, is used as plasminogen activator.

It is also preferred to use a polysulfated polysaccharide, in particular dextran sulfate or pentosan sulfate. The sulfated carbohydrate can comprise heparan sulfate, dermatan sulfate, dextan sulfate, chondroitin sulfate, pentosan sulfate, galactosan polysulfate, keratan sulfate, or mucopolysaccharide polysulfate and can be used, in a concentration of $10^{-8}$ to 1 mg/ml, in the assay mixture.

The activity of the plasminogen activator can be determined using a chromogenic substrate specific for this plasminogen activator. The change in the extinction caused by splitting off of the chromophore is measured using a spectrophotometric method. It is proportional to the concentration of the plasminogen activator.

Comparisons have shown good agreement between the protein C inhibitor determination according to the invention and a state of the art protein C inhibitor determination. The latter was carried out in the presence of activated protein C, from whose activity the protein C inhibitor concentration was determined.

The invention also relates to an agent for use in the method according to the invention, containing 0.1–5,000 IU/ml urokinase or 0.001–500 µg/ml tissue plasminogen activator, $10^{-7}$–$10^{-1}$ g/l dextran sulfate, $5\times10^{-5}$ to 5 mg/ml fibrinogen, 2–20 g/l of a degraded and chemically crosslinked gelatin, and a nonionic detergent in buffer solution. The urokinase used (ACTOSOLV®) consists of a mixture of low-molecular-mass (LMM; 33 kD) and high-molecular-mass (HMM: 54 kD) forms, the ratio of the urokinase activity in the HMM fraction pool to that in the LMM fraction pool being not less than 2.0. The potency of such urokinase is not less than 70,000 IU/mg of protein.

To prepare an agent which is suitable for use in the method according to the invention and which contains plasminogen activator, for example human urokinase is dissolved in a concentration of 0.1–5,000, preferably 1,000, IU/ml, or tissue plasminogen activator is dissolved in a concentration of 0.001–500, preferably 0.1– 10, µg/ml, in a buffer solution, preferably 25–250 mmol/l tris buffer solution, especially 50 mmol/l tris, pH 6–9, preferably pH 8.

An agent of this type contains a polysulfated polysaccharide, preferably dextran sulfate, in a concentration of $10^{-7}$–$10^{-1}$ g/l, preferably $1.5\times10^{-3}$ g/l, and fibrinogen in a concentration of $5\times10^{-5}$–5 mg/ml, preferably 0.25 mg/mL.

In addition, an agent of this type expediently contains 50–250 mmol/l, preferably 80–120 mmol/l, NaCl, 2– 20 g/l, preferably 10 g/l, of a degraded and chemically crosslinked gelatin, and 0.5–5 g/l, preferably 1 g/l, of a nonionic detergent.

The agent can, where appropriate, be stabilized by additives and freeze-dried.

The example which follows illustrates the invention:

EXAMPLE a) Preparation of an agent suitable for the method according to the invention Human urokinase (Actosolv®, Behringwerke AG, Marburg) was dissolved in 50 mmol/l tris buffer solution, pH 8. The final concentration of urokinase was 200 IU/ml.

$1.5 \times 10^{-3}$ g/l dextran sulfate (MW about 8,000, degree of sulfation about 20%), 0.25 mg/ml fibrinogen, 100 mmol/l NaCl, 10 g/l polygeline (Behringwerke AG, Marburg) and 1 g/l $^R$Triton×100 were added.

The urokinase can be replaced by 1 μg/ml tissue plasminogen activator (230 IU/ml).

b) Detection of protein C inhibitor in buffer solutions

100 μl of the agent described under a) were incubated with 50 μl of plasma at room temperature for 2 minutes. Addition of 500 μl of substrate solution (S2444 ®Kabi Vitrum, 0.3 mmol/l in 50 mmol/l tris buffer) was followed by a further incubation time of 30 minutes at 37° C. The substrate conversion was stopped by addition of 100 μl of 8.5 mol/l acetic acid, and the extinction of the sample was determined in a photometer (405 nm). The measured results were evaluated using a reference plot obtained by addition of urokinase to a buffer deficient in protein C inhibitor.

The measured urokinase concentration was then inversely proportional to the protein C inhibitor concentration. The volume of the urokinase reagent can be between 50 and 200 μl, preferably 100 μl. The incubation time of the reagent with the sample can be varied between 2 and 20 minutes.

c) Detection of protein C inhibitor in plasma via a chromogenic urokinase substrate or plasminogen and chromogenic plasmin substrate 100 μl of the agent described under a) were incubated with 50 μl of plasma at room temperature (23° C.) for 2 minutes. Addition of 100 μl of 0.5M sodium acetate buffer, pH 4.0, was followed by incubation at 37° C. for 20 minutes. The assay mixture was then neutralized by addition of 500 μl of substrate solution (S 2444, ®Kabi Vitrum, 0.3 mmol/l in 250 mmol/l tris buffer, pH 9.6). After a further incubation time of 30 minutes at 370° C., the substrate conversion was stopped by addition of 100 μl of 8.5 mol/l acetic acid, and the extinction of the sample was determined in a photometer (405 nm).

In a variation of this example, the chromogenic substrate S 2444 was replaced by plasminogen (2 CTA/ml) and the chromogenic plasmin substrate BCP 500 (0.3 mmol/l) in tris buffer (250 mmol/l, pH 9.6), and the final incubation time was shortened to 1 minute.

The measured results were evaluated as indicated in Example b). Plasma deficient in protein C inhibitor was used in place of the buffer solution deficient in protein C inhibitor. This buffer had been prepared by immunoadsorption on an anti-protein C-inhibitor-sepharose.

We claim:

1. A method for the functional determination of protein C inhibitor in a body fluid, which method comprises the steps of: (a) incubating a sample of said fluid with a urokinase comprising a mixture of a low-molecular-mass (LMM) form of about 33 kD molecular weight and a high-molecular-mass (HMM) form of about 54 kD molecular weight, and having a potency of not less than 70,000 IU/mg, in a concentration of 0.1–5,000 IU/ml, in the presence of a sulfated carbohydrate in a concentration of $10^{-8}$ to 1 mg/ml, the amounts of said urokinase and said sulfated carbohydrate being sufficient to give a readable signal of activity of said urokinase after inhibition by said protein C inhibitor, (b) determining the residual activity of said urokinase, and (c) from this residual activity of said urokinase, determining the amount of protein C inhibitor in said fluid by comparing said residual activity of said urokinase with that activity obtained with a standard solution of known concentration of protein C inhibitor.

2. The method as claimed in claim 1, wherein said sulfated carbohydrate comprises dextran sulfate.

3. The method as claimed in claim 1, wherein the sulfated carbohydrate is selected from the group consisting of heparin, dermatan sulfate, dextran sulfate, chondroitin sulfate, pentosan sulfate, galactosan polysulfate, keratan sulfate and mucopolysaccharide polysulfate.

4. The method as claimed in claim 1, which comprises determining the residual activity of said urokinase by means of a chromogenic substrate specific for said urokinase.

5. The method as claimed in claim 1, which comprises determining said residual activity of said urokinase by means of plasminogen and a chromogenic plasmin substrate.

6. The method as claimed in claim 1, which comprises determining the residual activity of urokinase at 20°–25° C.

7. The method as claimed in claim 1, which comprises determining the residual activity of urokinase in the presence of $5 \times 10^{-5}$–5 mg/ml fibrinogen.

8. A method for the functional determination of protein C inhibitor in a body fluid, which method comprises the steps of: (a) incubating a sample of said fluid with a urokinase comprising a mixture of a low-molecular-mass (LMM) form of about 33 kD molecular weight and of a high-molecular-mass (HMM) form of about 54 kD molecular weight, and having a potency of not less than 70,000 IU/mg, in a concentration of 0.1–5,000 IU/ml in the presence of a sulfated carbohydrate in a concentration of $10^{-8}$ to 1 mg/ml and of fibrinogen, the amounts of said urokinase and said sulfated carbohydrate being sufficient to give a readable signal of activity of said urokinase after inhibition by said protein C inhibitor, (b) measuring the residual activity of said urokinase, and (c) determining the amount of protein C inhibitor in said fluid by comparing said residual activity of said urokinase with that activity obtained with a standard solution of known concentration of protein C inhibitor.

9. A reagent for determining protein C inhibitor comprising 0.1–5,000 IU/ml urokinase, comprising a mixture of a low-molecular-mass (LMM) form of about 33 kD molecular weight and a high-molecular-mass (HMM) form of about 54 Kd molecular weight, and having a potency of not less than 70,000 IU/mg $10^{-7}$–$10^{-1}$ g/l a sulfated carbohydrate, $5 \times 10^{-5}$ to 5 mg/ml fibrinogen, and a nonionic detergent in a buffer solution of pH 6–9.

* * * * *